(12) United States Patent
Idiris et al.

(10) Patent No.: US 8,329,448 B2
(45) Date of Patent: Dec. 11, 2012

(54) YEAST HOST, TRANSFORMANT AND METHOD FOR PRODUCING HETEROLOGOUS PROTEINS

(75) Inventors: Alimjan Idiris, Tokyo (JP); Hideki Tohda, Tokyo (JP); Yuko Hama, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 728 days.

(21) Appl. No.: 12/025,138

(22) Filed: Feb. 4, 2008

(65) Prior Publication Data
US 2008/0206816 A1 Aug. 28, 2008

Related U.S. Application Data

(63) Continuation of application No. PCT/JP2006/315173, filed on Jul. 31, 2006.

(30) Foreign Application Priority Data

Aug. 3, 2005 (JP) ................................. 2005-225638
Jun. 8, 2006 (JP) ................................. 2006-160347

(51) Int. Cl.
*C12N 1/16* (2006.01)
*C12N 1/19* (2006.01)
*C12N 15/09* (2006.01)
*C12N 15/12* (2006.01)
*C12N 15/16* (2006.01)
*C12N 15/18* (2006.01)
*C12N 15/81* (2006.01)

(52) U.S. Cl. ................. 435/254.11; 435/69.1; 435/69.4; 435/255.1

(58) Field of Classification Search .......................... None
See application file for complete search history.

(56) References Cited

U.S. PATENT DOCUMENTS 5,919,654 A * 7/1999 Hama et al. .................. 435/69.1
6,235,499 B1 * 5/2001 Tohda et al. ................. 435/69.1
(Continued)

FOREIGN PATENT DOCUMENTS
EP 0 327 797 A1 8/1989
(Continued)

OTHER PUBLICATIONS

Meerman, H. J., et al., 1994, "Construction and characterization of a set of *E. coli* strains deficient in all known loci affecting the proteolytic stability of secreted recombinant proteins", Bio/Technology, vol. 12, pp. 107-110.*

(Continued)

*Primary Examiner* — Manjunath Rao
*Assistant Examiner* — William W Moore
(74) *Attorney, Agent, or Firm* — Oblon, Spivak, McClelland, Maier & Neustadt, L.L.P.

(57) ABSTRACT

The efficiency of production of a heterologous protein by a transformant of a yeast host is improved.
A method of constructing a host for expression of a foreign gene which comprises deleting or inactivating at least one gene selected from the protease-associated genes (especially, metalloprotease genes and serine protease genes) of *Schizosaccharomyces pombe*, a host in which the above-mentioned gene is deleted or inactivated, a transformant obtained by introducing a foreign gene into the host and a method of producing a heterologous protein using the transformant.
The protease-associated gene is at least one gene selected from the group consisting of psp3 (SPAC1006.01), is sxa2 (SPAC1296.03c), ppp51 (SPAC22G7.01c) and ppp52 (SPBC18A7.01) or at least two genes selected from the group consisting of metalloprotease genes and serine protease genes, especially, three genes psp3 (SPAC1006.01), isp6 (SPAC4A8.04) and ppp53 (SPAP14E8.04). A host in which four genes consisting of the above three genes and ppp16 (SPBC1711.12), or five genes consisting of the above four genes and ppp22 (SPBC14C8.03) are deleted or inactivated is preferred.

16 Claims, 7 Drawing Sheets

U.S. PATENT DOCUMENTS

| | | | |
|---|---|---|---|
| 6,342,375 B1* | 1/2002 | Olazaran et al. | 435/69.4 |
| 6,352,841 B1 | 3/2002 | Lehmbeck | |
| 7,723,098 B2* | 5/2010 | Tohda et al. | 435/254.2 |
| 2004/0110252 A1* | 6/2004 | Davey | 435/69.1 |
| 2004/0132192 A1* | 7/2004 | Thoda et al. | 435/483 |

FOREIGN PATENT DOCUMENTS

| | | |
|---|---|---|
| JP | 2776085 | 1/1993 |
| JP | 7-163373 | 6/1995 |
| JP | 10-215867 | 8/1998 |
| JP | 10-234375 | 9/1998 |
| JP | 11-192094 | 7/1999 |
| JP | 2000-136199 | 5/2000 |
| JP | 2000-262284 | 9/2000 |
| JP | 2001-500381 | 1/2001 |
| JP | 2004-507270 | 3/2004 |
| WO | WO 96/23890 | 8/1996 |
| WO | WO 97/12045 | 4/1997 |
| WO | WO9812300 | 3/1998 |
| WO | WO 02/101038 | 12/2002 |
| WO | WO 2004/090117 | 10/2004 |

OTHER PUBLICATIONS

Davey, J., et al., 1994, "Isolation and characterisation of krp, a dibasic endopeptidase required for cell viability in the fission yeast *Schizosaccharomyces pombe*", EMBO Journal, vol. 13, pp. S910-S921.*

Battersby, J.E., et al., 1994, "Diketopiperazine formation and N-terminal degradation in recombinant human growth hormone," International Journal of Peptide and Protein Research, vol. 44, No. 3, pp. 215-222.*

Copley, K.S., et al., 1998, "Expression, processing and secretion of a proteolytically-sensitive insect diuretic hormone by *Saccharomyces cerevisiae* requires the use of a yeast strain lacking the genes encoding the Yap3 and Mkc7 endoproteases found in the secretory pathway", Biochemical Journal, vol. 330, pp. 1333-1340.*

Ladds, G. et al., 2000, "Identification of proteases with shared functions to the proprotein processing protease Krp1 in the fission yeast *Schizosacchaomyces pombe*", Molecular Microbiology, vol. 38, No. 4, pp. 839-853.*

Wood, V., et al., 2002, "The genome sequence of *Schizosaccharomyces pombe*", Nature, vol. 415, pp. 871-880; and Corrigendum, Wood, V., et al., 2003, Nature, vol. 421, p. 94.*

GeneDB—*S.pombe*—SPAC1006.01, 2002.*
GeneDB—*S.pombe*—SPAC1296.03c, 2002.*
GeneDB—*S.pombe*—SPAC4A8.04, 2002.*
GeneDB—*S.pombe*—SPAC22G7.01c, 2002.*
GeneDB—*S.pombe*—SPAC23H4.09, 2002.*
GeneDB—*S.pombe*—SPAP14E08.04, 2002.*
GeneDB—*S.pombe*—SPBC1711.12, 2002.*
GeneDB—*S.pombe*—SPBC14C8.03, 2002.*
GeneDB—*S.pombe*—SPBC18A7.01, 2002.*

Ladds et al, Mol. Microbiol. (1996), 20(1) pp. 35-42.
Egel et al, Yeast (1994), 10(10) pp. 1347-1354.
Idiris et al, Yeast (2006), 23(2) pp. 83-89.
U.S. Appl. No. 12/129,413, filed May 29, 2008, Hirashima, et al.

Bi Kewei, et al., "Protease-deficient strains of fission yeast *Schizosaccharomyces pombe* for heterologous protein production", XXIst International Conference on Yeast Genetics and Molecular Biology, vol. 20, No. Supplement 1, XP-009106703, Jul. 2003, p. S320.

Alimjan Idiris, et al., "Enhanced productivity of protease-sensitive heterologous proteins by disruption of multiple protease genes in the fission yeast *Schizosaccharomyces pombe*", Applied Microbiology and Biotechnology, vol. 73, No. 2, XP-002498506, Jun. 27, 2006, pp. 404-420.

* cited by examiner

FIG. 7

YEAST HOST, TRANSFORMANT AND METHOD FOR PRODUCING HETEROLOGOUS PROTEINS

TECHNICAL FIELD

The present invention relates to an improved eukaryotic host microorganism in which part of the chromosomes are modified for the purpose of improving the productivity of a heterologous protein by a transformant of the eukaryotic host microorganism, a method of constructing the host, a transformant of the host and a method of producing a protein using the transformant, in particular, wherein the eukaryotic microorganism is Schizosaccharomyces pombe (hereinafter referred to as S. pombe) called a fission yeast.

BACKGROUND ART

Recombinant DNA technology is used for production of heterologous proteins in various host microorganisms and animals including Escherichia coli (hereinafter referred to as E. coli). The target products are various biogenous proteins (herein, inclusive of polypeptides), and many of them have already been produced industrially for medical and other uses so far.

Among various hosts developed for production of heterologous proteins, yeasts seem favorable for expression of animal and plant proteins because of their eukaryotic similarity in the transcription and translation systems to animals and plants, and the baker's yeast (Saccharomyces cerevisiae) is a widely used host.

Among yeasts, S. pombe is known to be close to animal cells in nature as is evident from the fact that it grows by fission not by budding as a result of the different evolution process it has followed since it diverged from other yeasts at early stages. Therefore, the use of S. pombe as the host for expression of heterologous proteins is expected to provide a gene product closer to its natural form in animal cells.

Though studies of gene expression in S. pombe are delayed, the recent discovery of potent promoters functional in S. pombe has accelerated the development of expression systems using S. pombe as the host, and various improvements have been added to expression vectors to develop more stable and efficient expression systems (Patent Documents 1 to 8). As a result, expression systems using S. pombe as the host show high production efficiency now.

Production systems for heterologous proteins using eukaryotic microorganisms such as yeasts can be realized easily by conventional microbiological techniques and recombinant DNA technology with high productivity. Large cultures are already available and are acceleratingly used for actual production. Even after the scale is enlarged for actual production, cells retain the high production efficiency per cell obtained in the laboratory.

Considering that cost reduction is often demanded in actual production, it is necessary to improve the production efficiency of heterologous proteins through improvement in cell growth efficiency, suppression of degradation of the heterologous protein of interest, more efficient eukaryotic modifications in the microorganisms or more efficient utilization of the nutrition sources. For example, increase in the conversion of the carbon sources added to the medium for culture growth into the heterologous protein of interest is expected to drastically improve cell growth efficiency and therefore production efficiency of the heterologous protein, because efficient utilization of the carbon sources in the medium for production of the heterologous protein of interest seems to be sacrificed for their consumption by metabolic systems unnecessary for cell growth or production of the heterologous protein of interest (such as the ethanol fermentation system for production of ethanol).

Therefore, attempts have been made to improve production efficiency of heterologous proteins by a host by deleting or inactivating part or all of the genome of the host unnecessary or detrimental to production of heterologous proteins (Patent Documents 9 and 10).

The present inventors reported about the invention described in the patent applications from which the present application claims the earlier priority date, in an article published after the earlier priority application (before the later priority date) (Non-patent Document 1)

Patent Document 1: Japanese Patent No. 2776085
Patent Document 2: JP-A-07-163373
Patent Document 3: JP-A-10-215867
Patent Document 4: JP-A-10-234375
Patent Document 5: JP-A-11-192094
Patent Document 6: JP-A-2000-136199
Patent Document 7: JP-A-2000-262284
Patent Document 8: WO96/023890
Patent Document 9: WO02/101038
Patent Document 10: WO04/090117
Non-patent Document 1: Yeast, vol. 23, pp. 83-99, 2006

DISCLOSURE OF THE INVENTION

Problems that the Invention is to Solve

The use of an improved host in which all or part of the regions in the genome detrimental to production of heterologous proteins have been deleted or inactivated improves the efficiency of production of heterologous proteins as disclosed in the above-mentioned patent documents. However, it is necessary to further investigate where on the chromosomes (especially, which genes) to modify in order to attain a higher production efficiency because efficiency of production of heterologous proteins depends on which parts of the chromosomes (especially which genes) are deleted or inactivated in what combinations.

Means of Solving the Problems

Under the above-mentioned circumstance, the present inventors studied from the above-mentioned aspects, and, as a result, found that deletion or inactivation of at least one protease-related gene drastically improves the production efficiency of heterologous proteins. Namely, the present invention provides:

1. A method of constructing an improved Schizosaccharomyces pombe host for expression of a recombinantly introduced foreign gene, which is characterized by deleting or inactivating at least one gene selected from the groups consisting of genes encoding serine proteases (serine protease gene family), genes encoding amino peptidases (amino peptidase gene family), genes encoding carboxy peptidases (carboxy peptidase gene family) and genes encoding dipeptidases (dipeptidase gene family), as a target gene.

2. The method according to claim 1, wherein the target gene is at least one gene selected from the group consisting of psp3 (SPAC1006.01), sxa2 (SPAC1296.03c), ppp51 (SPAC22G7.01c) and ppp52 (SPBC18A7.01).

3. A method of constructing an improved Schizosaccharomyces pombe host for expression of a recombinantly introduced foreign gene, which is characterized by deleting or inactivating two or more gene selected from the groups consisting of genes encoding metalloproteases (metalloprotease gene family), genes encoding serine proteases (serine protease gene family), genes encoding cysteine proteases (cysteine protease gene family) and genes encoding aspartyl proteases (aspartyl protease gene family), as target genes.

4. The method according to 3 mentioned above, wherein the two or more genes are a total of at least three genes consisting of at least one gene selected from the metalloprotease gene family and at least two genes selected from the serine protease gene family.

5. The method according to 3 or 4 mentioned above, wherein the two or more genes are a total of at least three genes consisting of at least one gene selected from the group consisting of cdb4 (SPAC23H4.09), ppp22 (SPBC14C8.03) and ppp53 (SPAP14E8.04) and at least two genes selected from the group consisting of isp6 (SPAC4A8.04), ppp16 (SPBC1711.12), psp3 (SPAC1006.01) and sxa2 (SPAC1296.03c).

6. The method according to any one of 1 to 5 mentioned above, wherein the genes are deleted or inactivated by replacing the ORF(s) (open reading frame(s)) of the gene(s) with marker genes.

7. An improved *Schizosaccharomyces pombe* host for expression of a recombinantly introduced foreign gene, in which at least one gene selected from the group consisting of psp3 (SPAC1006.01), sxa2 (SPAC1296.03c), ppp51 (SPAC22G7.01c) and ppp52 (SPBC18A7.01) is deleted or inactivated.

8. An improved *Schizosaccharomyces pombe* host for expression of a recombinantly introduced foreign gene, in which two or more genes selected from the group consisting of genes encoding metalloproteases (metalloprotease gene family), genes encoding serine proteases (serine protease gene family), genes encoding cysteine proteases (cysteine protease gene family) and genes encoding aspartyl proteases (aspartyl protease gene family).

9. The host according to 8 mentioned above, wherein the two or more genes are a total of at least three genes consisting of at least one gene selected from the metalloprotease gene family and at least two genes selected from the serine protease gene family.

10. The host according to 8 or 9 mentioned above, wherein the two or more genes are a total of at least three genes consisting of at least one gene selected from the group consisting of cdb4 (SPAC23H4.09), ppp22 (SPBC14C8.03) and ppp53 (SPAP14E8.04) and at least two genes selected from the group consisting of isp6 (SPAC4A8.04), ppp16 (SPBC1711.12), psp3 (SPAC1006.01) and sxa2 (SPAC1296.03c).

11. A transformant obtained by introducing a gene encoding a heterologous protein into the host as defined above in any one of 7 to 10.

12. The transformant according to 11 mentioned above, wherein a secretion signal gene is introduced with the gene encoding a heterologous protein.

13. A method of producing a heterologous protein, which comprises culturing the transformant as defined above in 11 or 12 to allow it to produce the heterologous protein, and recovering the heterologous protein.

14. A method of producing a heterologous protein, which comprises culturing the transformant as defined above in 12 to allow it to produce the heterologous protein and secret the heterologous protein in the culture, and recovering the heterologous protein from the culture.

15. The method according to claim 13 or 14, wherein according to 13 mentioned above, wherein the heterologous protein is human growth hormone (hGH).

Effects of the Invention

The present invention is based on the discovery that gene-disrupted host strains constructed by deleting or inactivating (hereinafter sometimes referred to collectively as disrupting) one or more protease-related genes in the fission yeast *S. pombe* putatively associated with degradation of heterologous proteins can produce heterologous proteins more efficiently when transformed. These protease-related gene disruptants can be used widely for production of protease-sensitive heterologous proteins.

BRIEF DESCRIPTION OF THE DRAWINGS

FIG. 3 (A) SDS-PAGE showing r-hGH secretions from a transformant ARC001 (hGH) at various times. (B) SDS-PAGE showing r-hGH secretions from a transformant ARC001 (hGH) in the presence of protease inhibitors in culture at various times.

BEST MODE FOR CARRYING OUT THE INVENTION

In the present invention, the improved host is a *S. pombe* strain. Hereinafter, the host means a *S. pombe* strain unless otherwise noted. In the present invention, protease-related genes include genes which are presumed to be protease-related genes from their DNA sequences (or from the structures or amino acid sequences of the polypeptides or proteins encoded by the genes).

When a transformant produces a heterologous protein in culture, part of the genome is unnecessary or detrimental to production of the heterologous protein. The part of the genome may or may not be a gene. It is believed that a lot of such unnecessary or detrimental genes exist in a genome.

It is generally presumed that some protease-related genes tend to inhibit production of a heterologous protein. Because the heterologous protein is a product fundamentally unnecessary to the host, the transformant tends to degrade the produced heterologous protein by proteases. Therefore, degradation of the heterologous protein is considered as a factor of reduction in the production efficiency of the heterologous protein. However, not all proteases are unnecessary or detrimental to the host, and some have unfavorable effect when inactivated. Therefore, the present invention resides in the discovery that selective disruption of genes which produce unnecessary or detrimental proteases improves production efficiency of a heterologous protein.

In the present invention, the efficiency of production of a heterologous protein by a transformant is successfully improved by deleting or inactivating at least one protease-related gene selected from the group consisting of four protease-related gene families, the serine protease gene family, the amino peptidase gene family, the carboxypeptidase gene family and the dipeptidase gene family, as the target(s) in the genome unnecessary or detrimental to production of the heterologous protein. In the improved yeast host of the present invention, at least one gene selected from the above-mentioned four groups of protease-related genes is deleted or inactivated, and further, at least one other gene may be deleted or inactivated.

The target gene selected from the above-mentioned four protease-related gene families is preferably at least one gene encoding a protease or a putative protease protein selected from psp3 (SPAC1006.01), sxa2 (SPAC1296.03c), ppp51 (SPAC22G7.01c) and ppp52 (SPBC18A7.01). psp3 (SPAC1006.01) and sxa2 (SPAC1296.03c) are classified as serine protease genes, while ppp51 (SPAC22G7.01c) and ppp52 (SPBC18A7.01) are genes putatively encoding amino peptidase proteins (amino peptidase genes). They are also classified as metalloprotease genes (genes of proteases containing metal ions).

However, the above-mentioned object is often difficult to attain satisfactorily by deleting or inactivating only one protease-related gene. Deletion or inactivation of a single protease-related gene can be insufficient (i.e., is not versatile to improve various heterologous proteins). Further, because various proteases in a living organism often have overlapping functions, deletion or inactivation of a single protease-related gene may improve productivity somewhat, but not drastically. Therefore, in the present invention, it is preferred to delete or inactivate at least two, preferably at least three genes. Deletion or inactivation of the two or more protease-related genes of choice drastically improves production efficiency of a heterologous protein.

Therefore, in the present invention, the efficiency of production of a heterologous protein by a transformant is successfully improved also by deleting or inactivating at least two genes selected from the group consisting of four protease-related gene families, the metalloprotease gene family, the serine protease gene family, the cysteine protease gene family and the aspartyl protease gene family, as the targets in the genome unnecessary or detrimental to production of the heterologous protein. In the improved yeast host of the present invention, at lease two genes selected from the above-mentioned four groups of protease-related genes, and, further, at least one other gene may be deleted or inactivated.

The construction method of the present invention comprising deleting or inactivating two or more genes selected form the above-mentioned four groups of protease-related genes and the host of the present invention in which such two or more genes are deleted or inactivated will be described. Deletion or inactivation of at least one gene can be carried out similarly.

The two or more genes to be deleted or inactivated which are selected from the above-mentioned four protease-related gene families may be two or more genes selected from the same single gene family or from different gene families. In the latter case, they may be a total of three or more genes consisting of at least two genes selected from one family and at least one gene selected from another family. Further, at least two genes selected from the above-mentioned four protease-related gene families and a gene selected from another gene family (which may not be protease-related genes) may be deleted or inactivated in combination.

The target protease-related genes may be deleted or inactivated by known methods. Further, the regions of the protease-related genes to be deleted or inactivated may be the open reading frames (ORFS) or the expression regulatory regions. The method for carrying out the deletion or inactivation is preferably the PCR-mediated homologous recombination (Yeast, vol. 14, pp. 943-951, 1998), which was used later in the Examples, but is not restricted to it.

The deletion or inactivation of protease-related genes may be deletion of the entire genes or inactivation of the genes by partial deletion. The inactivation of protease-related genes means not only partial deletion of the genes but also modification of the genes without deletion. Further, it may be insertion of other genes or DNA into the base sequences of the protease-related genes. In either case, the inactivated protease-related genes encode inactive proteins or are unable to be transcribed or translated. When two or more genes for the same protease are present in the cell, all the genes may be deleted, or some of the genes may be left as long as the protease encoded by the gene shows reduced activity in the cell.

The genes in the protease-related gene families in the present invention are at least two genes selected from the group consisting of genes encoding metalloproteases (the metalloprotease gene family), genes encoding serine proteases (the serine protease gene family), genes encoding cysteine proteases (the cysteine protease gene family) and genes encoding aspartyl proteases (the aspartyl protease gene family), preferably at least two genes selected from the metalloprotease gene family and the serine protease gene family. A combination of at least one gene in the two gene families and at least one gene selected from the cysteine protease gene family and the aspartyl protease gene family is also preferred. Examples of these genes are given below (see Table 1, which appears later).

The metalloprotease gene family: cdb4 (SPAC23H4.09), mas2 (SPBC18E5.12c), pgp1 (SPCC1259.10), ppp20 (SPAC4F10.02), ppp22 (SPBC14C8.03), ppp51 (SPC22G7.01c), ppp52 (SPBC18A7.01) and ppp53 (SPAP14E8.04).

The serine protease gene family: isp6 (SPAC4A8.04), ppp16 (SPBC1711.12), psp3 (SPAC1006.01) and sxa2 (SPAC1296.03c).

The cysteine protease gene family: ppp80 (SPAC19B12.08), pca1 (SPCC1840.04), cut1 (SPCC5E4.04) and gpi8 (SPCC11E10.02c).

The aspartyl protease gene family: sxa1 (SPAC26A3.01), ypsl (SPCC1795.09) and ppp81 (SPAC25B8.17).

In the present invention, the protease-related genes as the targets for deletion or inactivation are selected from the metalloprotease gene family and the serine protease gene family, and are preferably a combination of two or more genes selected from the two gene families or a combination of at least one gene selected from the two gene families and at least one gene selected from the other families. The former combination is particularly preferred. More preferably, they are a total of at least three genes consisting of at least one gene selected from the metalloprotease gene family and at least two genes selected from the serine protease gene family. When the targets are at least four genes, they preferably consist of at least 50%, in number, of genes in the serine protease gene family and at least one gene (preferably at least two genes) in the metalloprotease gene family, and other genes, if any, in the cysteine protease gene family.

The target genes in the metalloprotease gene family are preferably cdb4 (SPAC23H4.09), pgp1 (SPCC1259.10), ppp20 (SPAC4F10.02), ppp22 (SPBC14C8.03), ppp52 (SPBC18A7.01) and ppp53 (SPAP14E8.04), and particularly cdb4 (SPAC23H4.09), ppp22 (SPBC14C8.03) and ppp53 (SPAP14E8.04).

The target genes in the serine protease gene family are preferably isp6 (SPAC4A8.04), ppp16 (SPBC1711.12), psp3 (SPAC1006.01) and sxa2 (SPAC1296.03c).

The target gene in the other gene families is preferably ppp80 (SPAC19B12.08).

More specifically, the target genes are preferably a combination of a total of at least three genes consisting of at least one gene selected from the group consisting of cdb4 (SPAC23H4.09), ppp22 (SPBC14C8.03) and ppp53 (SPAP14E8.04) and at least two genes selected from the group consisting of isp6 (SPAC4A8.04), ppp16 (SPBC1711.12), psp3 (SPAC1006.01) and sxa2 (SPAC1296.03c), particularly preferably a combination of a total of at least three genes consisting of at least one gene selected from the group consisting of ppp53 (SPAP14E8.04) and cdb4 (SPAC23H4.09), and isp6 (SPAC4A8.04) and psp3 (SPAC1006.01). For example, at least three genes comprising psp3 (SPAC1006.01), isp6 (SPAC4A8.04) and ppp53 (SPAP14E8.04) are preferred (see Table 3, which appears later).

A particularly preferred combination consists of at least four genes comprising ppp53 (SPAP14E8.04), isp6 (SPAC4A8.04), psp3 (SPAC1006.01) and ppp16 (SPBC1711.12), more preferably at least five genes comprising ppp53 (SPAP14E8.04), isp6 (SPAC4A8.04), psp3 (SPAC1006.01), ppp16 (SPBC1711.12) and ppp22 (SPBC14C8.03). When the targets are at least 6 genes, it is further preferred to combine sxa2 (SPAC1296.03c) with these five genes (see Table 3, which appears later).

The maximum number of genes to be disrupted is not limited, as long as the object of the present invention is attained. However, disruption of too many genes tends to produce unfavorable effects such as a low growth rate. In the present invention, the relative growth rate of the gene-disrupted host (the growth rate in relation to the intact S. pombe strain before gene disruption) is preferably at least 0.6, particularly at least 0.8. In the present invention, it has little significance to disrupt genes whose disruption hardly improves the expression efficiency of foreign genes, though their disruption may not reduce the growth rate so much. For these reasons, it is appropriate to estimate that the maximum number of genes to be disrupted is 20, preferably 10.

The present invention further provides a host (i.e., a transformant) carrying a gene (hereinafter referred to as a foreign gene) encoding a protein extrinsic to the host (hereinafter referred to as a heterologous protein) recombinantly introduced therein, and a method of producing a heterologous protein which comprises culturing the transformant to allow it to produce the heterologous protein and recovering the heterologous protein.

Though there are no restrictions on the heterologous protein to be produced by the improved host of the present invention, it is preferably a protein produced by multicellular organisms such as animals and plants, especially a protein produced by a mammal (inclusive of human) such as human growth hormone. Such a protein is rarely obtained with high activity from a prokaryotic host microorganism such as E. coli, but is usually obtained from an animal cell line such as CHO used as the host with low production efficiency. The use of the genetically modified eukaryotic host microorganism of the present invention is considered to solve these problems.

For genetic transformation using yeasts as the host, various expression systems, especially expression vectors and expression vectors with a secretion signal gene, which allow efficient and stable production of heterologous proteins, have been developed, and they are widely available to genetically transform the improved host of the present invention. For example, expression systems disclosed in Japanese Patent No. 2776085, JP-A-07-163373, JP-A-10-215867, JP-A-10-234375, JP-A-11-192094, JP-A-2000-136199, JP-A-2000-262284 and WO96/023890 can be widely used in the method of producing is a heterologous protein of the present invention.

Now, the present invention will be described in further detail by reference to specific Examples. The following Examples exemplify deletion of protease-related genes in S. pombe through replacement with marker genes, and hereinafter deletion of genes will be referred to as disruption.

Hereinafter, percentages (%) are expressed in weight percent unless otherwise noted.

EXAMPLE 1

Transformation of S. pombe Strains and Cultivation Conditions

All S. pombe strains were derived from ARC001 (h⁻leu1-32) and ARC010 (h⁻leu1-32ura4-D18) and transformed by the lithium acetate transformation method (Okazaki K et al. 1990, Nucleic Acids Res 18:6485-8489.). Transformant mixtures were plated onto MMA (minimal medium agar, from Qbiogene) or MMA+Leu (supplemented with leucine) and incubated at 32° C. for 3 to 4 days. The cultures were grown in YES medium [yeast extract with supplements, 0.5% Bactoyeast extract, (Becton, Dickinson and Company), 3% glucose and SP supplements (from Qbiogene)], YPD medium [1% Bactoyeast extract, 2% Bacto peptone (Becton, Dickinson and Company) and 2% glucose] and SDC-Ura and SDC-Ura-Leu media (synthetic complete dextrose media lacking uracil or both uracil and leucine from Qbiogene).

<Preparation of Recombinant DNA>

Recombinant DNA procedures were followed as described in Sambrook et al. (Sambrook J et al. 1989. Molecular Cloning. A Laboratory Manual. $2^{nd}$ ed. Cold Spring Harbor Laboratory Press, Cold Spring Harbor). Restriction enzymes and DNA modification enzymes were obtained from Takara Bio, Toyobo, Nippon Gene and Roche Diagnostics. Gene disruption fragments were prepared by PCR amplification using KOD Dash DNA polymerase (TOYOBO). All enzymes were used according to the suppliers' protocols. Escherichia coli strain DH5 (Toyobo) was used for plasmid preparation. DNA sequencing was carried out with the DNA sequencer ABI Prism 3100 genetic analyzer (Applied Biosystems). Yeast genomic DNA was prepared using a DNeasy genomic DNA kit (Qiagen).

<Construction of Protease Gene-Deficient S. pombe Strains>

62 genes were listed as putative S. pombe proteases (ppp) on the basis of the chromosome sequence data (Wood et al., 2002, http://_www.sanger.ac.uk./Projects/S_pombe/) and the S. pombe Gene DB (http://_www.genedb.org/genedb-_pombe/). Table 1 shows known and putative S. pombe proteases. The ORFs (open reading frames) of the listed genes were disrupted by PCR-mediated homologous recombination (Bahler J et al. 1998. Yeast 14: 943-91) using a ura4 gene cassette as the selection marker. 200 to 300-bp sequences flanking the 5'- and 3'-termini of each target ORF were amplified from the genomic DNA of the parental S. pombe strain ARC001 by two separate PCRs using an appropriate gene adapter pair designed so that the 5' and 3' termini fuse separately. Then, by fusion extension PCR, the ura4 gene cassette was sandwiched between each pair of the resultant fusion PCR products to obtain vectors for protease gene disruption (hereinafter referred to as gene disruption vectors).

S. pombe strain ARC010 was transformed with the gene disruption vectors. The transformed cells were grown on minimal medium, and colonies of uracil-unrequiring strains formed in the minimal medium (MMA+Leu plates) were obtained. Disruption of protease genes in the strains was confirmed by colony PCR and DNA sequencing.

TABLE 1

Table 1. *S. pombe* putative proteases selected for gene disruption.

| No. | Gene | Systematic name | Description of gene products | Protease family | *S. cerevisiae* homologue | Deficient strain name |
|---|---|---|---|---|---|---|
| 1 | ape1 | SPBC1921.05 | Aminopeptidase I | M1 | APE2 | MGF0006 |
| 2 | cdb4 | SPAC23H4.09 | Metallopeptidase | M24X | no | MGF0071 |
| 3 | cps1 | SPAC24C9.08 | Vacuolar carboxypeptidase S* | M20E | CPS1 | MGF0014 |
| 4 | cpy1 | SPAC19G12.10C | Carboxypeptidase Y | S10 | PRC1 | MGF0030 |
| 5 | cut1 | SPCC5E4.04 | Separin, (caspase-like protease) | C50 | ESP1 | no disruption |
| 6 | gpi8 | SPCC11E10.02c | GPI anchor biosynthesis protease | C13 | GP18 | no disruption |
| 7 | isp6 | SPAC4A8.04 | Subtilase-type proteinase* | S8A | PRB1 | MGF0056 |
| 8 | krp1 | SPAC22E12.09C | Kexin, (dibasic processing endoprotease) | S8B | KEX2 | lethal** |
| 9 | mas2 | SPBC18E5.12C | Mitochondrial processing peptidase a | M16B | MAS2 | MGF0029 |
| 10 | mde10 | SPAC17A5.04C | Zinc metallopeptidase* | M12B | no | MGF0018 |
| 11 | oct1 | SPAC1F3.10C | Mitochondrial intermediate peptidase* | M3A | OCT1 | MGF0037 |
| 12 | pca1 | SPCC1840.04 | Cysteine protease* | C14 | YOR197W | MGF0058 |
| 13 | pgp1 | SPCC1259.10 | Endopeptidase* | M22 | YDL104C | MGF0034 |
| 14 | pgp2 | SPBC16D10.03 | Glycoprotease family | M22 | KAE1 | no disruption |
| 15 | psp3 | SPAC1006.01 | Subtilase-type peptidase* | S8A | PRB1 | MGF0031 |
| 16 | qcr1 | SPBP23A10.15C | Mitochondrial processing peptidase β | M16B | MAS1 | MGF0025 |
| 17 | qcr2 | SPCC613.10 | Mitochondrial signal processing protease | M16B | YPR191W | MGF0157 |
| 18 | sxa1 | SPAC26A3.01 | Aspartic proteinase | A1 | no | MGF0005 |
| 19 | sxa2 | SPAC1296.03C | Serine carboxypeptidase* | S10 | no | MGF0008 |
| 20 | yps1 | SPCC1795.09 | Aspartic proteinase* | A1 | YPS1 | MGF0004 |
| 21 | ppp10 | SPAC1687.02 | CAAX prenyl protease 2* | U48 | RCE1 | no disruption |
| 22 | ppp11 | SPAC3H1.05 | CAAX prenyl protease 1* | M48 | STE24 | MGF0019 |
| 23 | ppp16 | SPBC1711.12 | Dipeptidyl peptidase* | S9C | no | MGF0020 |
| 24 | ppp17 | SPCC965.12 | Dipeptidase* | M19 | no | MGF0021 |
| 25 | ppp18 | SPAC13A11.05 | Cytosol aminopeptidase | M17 | no | MGF0011 |
| 26 | ppp20 | SPAC4F10.02 | Aspartyl aminopeptidase* | M18 | APE1 | MGF0007 |
| 27 | ppp21 | SPAC14C4.15C | Dipeptidyl aminopeptidase | S9B | DAP2 | MGF0012 |
| 28 | ppp22 | SPBC14C8.03 | Methionine metallopeptidase* | M24A | MAP2 | MGF0022 |
| 29 | ppp23 | SPBC3E7.10 | Methionine aminopeptidase* | M24A | MAP1 | MGF0023 |
| 30 | ppp28 | SPBC337.07C | Carboxypeptidase* | M14A | ECM14 | MGF0013 |
| 31 | ppp33 | SPBC16G5.09 | Serine carboxypeptidase* | S10 | KEX1 | MGF0009 |
| 32 | ppp34 | SPACUNK4.12C | Zinc-protease* | M16A | STE23 | MGF0015 |
| 33 | ppp36 | SPCC965.04C | Metallopeptidase* | M41 | YME1 | MGF0017 |
| 34 | ppp37 | SPBC119.17 | Zinc metallopeptidase* | M16C | YDR430C | MGF0032 |
| 35 | ppp39 | SPAC22F3.06C | ATP-dependent protease* | S16 | YBL022C | MGF0033 |
| 36 | ppp43 | SPAC12B10.05 | Metallopeptidase* | M24B | YER078C | MGF0038 |
| 37 | ppp44 | SPAC3A11.10C | Microsomal dipeptidase* | M19 | no | MGF0039 |
| 38 | ppp45 | SPBC1685.05 | Serine protease* | S1C | YNL123W | MGF0057 |
| 39 | ppp50 | SPACUNK4.08 | Dipeptidyl aminopeptidase | S9B | DAP2 | MGF0059 |
| 40 | ppp51 | SPAC22G7.01C | Aminopeptidase* | M24B | YLL029W | MGF0062 |
| 41 | ppp52 | SPBC18A7.01 | Aminopeptidase* | M24B | no | MGF0144 |
| 42 | ppp53 | SPAP14E8.04 | Zinc metallopeptidase* | M48B | YKR087C | MGF0063 |
| 43 | ppp54 | SPAC3H1.02C | Zinc metallopeptidase* | M16C | YOL098C | MGF0068 |
| 44 | ppp57 | SPAC607.06C | Zinc metallopeptidase* | M10B | Y1L108W | MGF0069 |
| 45 | ppp58 | SPBC1198.08 | Metallopeptidase* | M20A | YFR044C | MGF0065 |
| 46 | ppp59 | SPBC354.09C | Metalloprotease* | M28X | YJR126C | MGF0066 |
| 47 | ppp60 | SPCC1919.12C | Metalloprotease* | M28X | YBR074W | MGF0067 |
| 48 | ppp61 | SPCC1259.02C | Metallopeptidase* | M28X | YBR074W | no disruption |
| 49 | ppp62 | SPAP8A3.12C | Tripeptidylpeptidase* | S8A | no | MGF0226 |
| 50 | ppp63 | SPBC23E6.05 | Metallopeptidase* | M24X | YDR101C | MGF0070 |
| 51 | ppp67 | SPBC2D10.07C | Mitochondrial protease subunit 2 | S26A | IMP2 | no disruption |
| 52 | ppp68 | SPBC336.13C | Mitochondrial protease subunit 1 | S26A | IMP2 | MGF0072 |
| 53 | ppp69 | SPBC1685.03 | Signal sequence processing peptidase | S26B | SEC11 | no disruption |
| 54 | ppp72 | SPBC13E7.11 | Mitochondrial signal processing protease | S54 | PCP1 | MGF0088 |
| 55 | ppp73 | SPBP4H10.10 | Mitochondrial signal processing protease | S54 | PCP1 | MGF0089 |
| 56 | ppp75 | SPCC790.03 | Rhomboid family protease | S54 | YPL246C | MGF0153 |
| 57 | ppp76 | SPBC543.09 | Mitochondrial signal processing protease | M41 | YMR089C | no disruption |
| 58 | ppp78 | SPCC757.05c | Metallopeptidase | M20A | no | MGF0154 |
| 59 | ppp79 | SPAC19B12.06c | Rhomboid family protease | S54 | YPL246C | MGF0158 |
| 60 | ppp80 | SPAC19B12.08 | Peptidase* | C54 | YNL223W | MGF0159 |
| 61 | ppp81 | SPAC25B8.17 | Signal peptide peptidase | A22B | YKL100C | MGF0160 |
| 62 | ppp85 | SPCC1322.05c | Metalloprotease* | M1 | YNL045W | no disruption |

*Putative proteases.
**Ref.: Davey et al., 1994

<Measurement of Cell Growth Rate>

Figure 1:
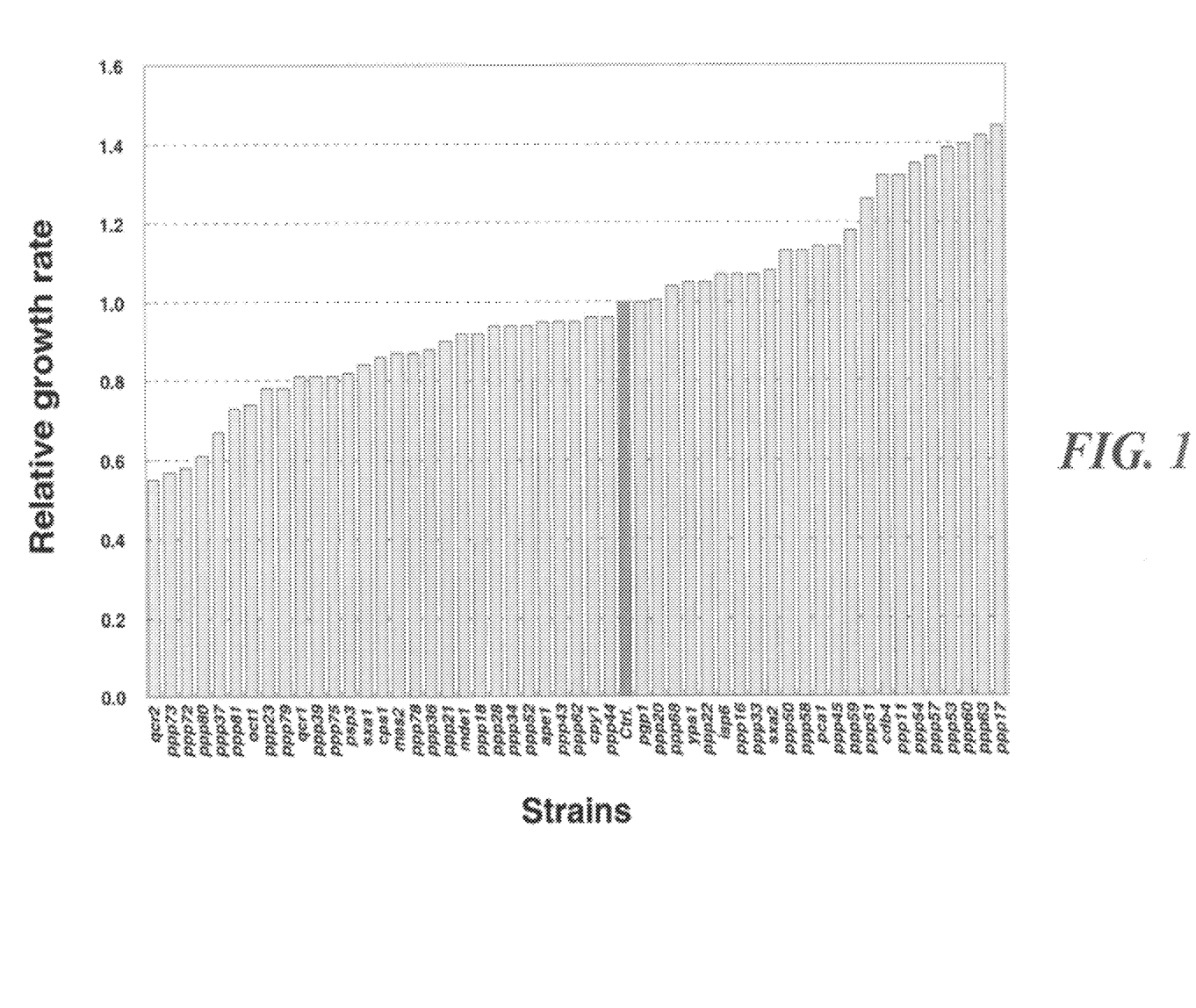
FIG. 1 A graph showing the relative growth rates of protease-related gene disruptants from *S. pombe*.

The growth rates of the resulting protease gene-deficient *S. pombe* strains were measured. Growth curves for the *S. pombe* strains were obtained using a biophotorecorder (TN-1506, Advantec). Cells were cultured in 5 ml YTS medium in L-tubes at 32° C. with shaking. Turbidity was monitored every 5 minutes at an absorbance of 660 nm. The relative maximum growth rates ($\mu_{max}$) of 52 protease disruptants were calculated using the $\mu_{max}$ value (0.26-0.30/H) for ARC001 strain as a control. FIG. 1 shows the relative maximum growth rates of the protease gene disruptants.

The results in FIG. 1 indicate that some protease genes affected cell growth rates. For example, disruption of nine protease genes (qcr2, oct1, ppp23, ppp37, ppp72m ppp73, ppp79 and ppp81) resulted in an over 20% decrease in $\mu_{max}$ as compared with the ARC001 control. A decrease exceeding 40% was obtained by deleting three mitochondrial signal processing proteases (qcr2, ppp72 and ppp73), indicating that all these protease genes are very important in the cell respiration process in *S. pombe* and that their disruption does not favor protein expression. Such growth rate reductions hinder efficient protein production. On the other hand, a $\mu_{max}$ increase exceeding 20% was obtained with disruption of cdb4, ppp11, ppp17, ppp51, ppp54, ppp57, ppp60 and ppp63, indicating that such growth rate increases do not hinder protein production.

EXAMPLE 2

Construction of r-hGH-Producing Transformant ARC001 (hCH)

A multicassette vector for secretory expression of r-hGH was prepared and used to construct a r-hGH-producing transformant ARC001 (hGH). A 594-bp hGH-ORF was artificially synthesized (Gene. Art) according to a codon table (highly biased) favorable for translation in *S. pombe* obtained from the ORF sequences of the high-expression genes, adh, tpi and gdp1, in *S. pombe*. By using restriction enzymes AflII and BamHI, from the integrative vector pXL4 (Isoai et al., 2002 Biotechnol Bioeng 80: 22-32.), the synthetic hGH gene fragment was integrated with the frame with a downstream P3 secretion signal sequence (WO96/023890). A multicassette expression vector, pTL2P3hGHhb(M5)-8XL, carrying eight tandem copies of the hGH expression cassette (hCMV-promoter/P3-signal/hGH-ORF/terminator) was then constructed as previously described (Ikeda et al., 2004 J. Biosci Bioeng 98: 366-373). Transformation was done by inserting the eight tandem copies of the hGH expression cassette from the expression vector into the lue1 locus in the protease-deficient *S. pombe* strains obtained as described previously. After 2 to 3 days of cultivation in SDC-Leu-Ura, leucine-unrequiring strains were harvested and incubated again in YPD medium (in 24-well plates) at 32° C. with shaking, and then secretion of r-HGH was confirmed.

Figure 2:
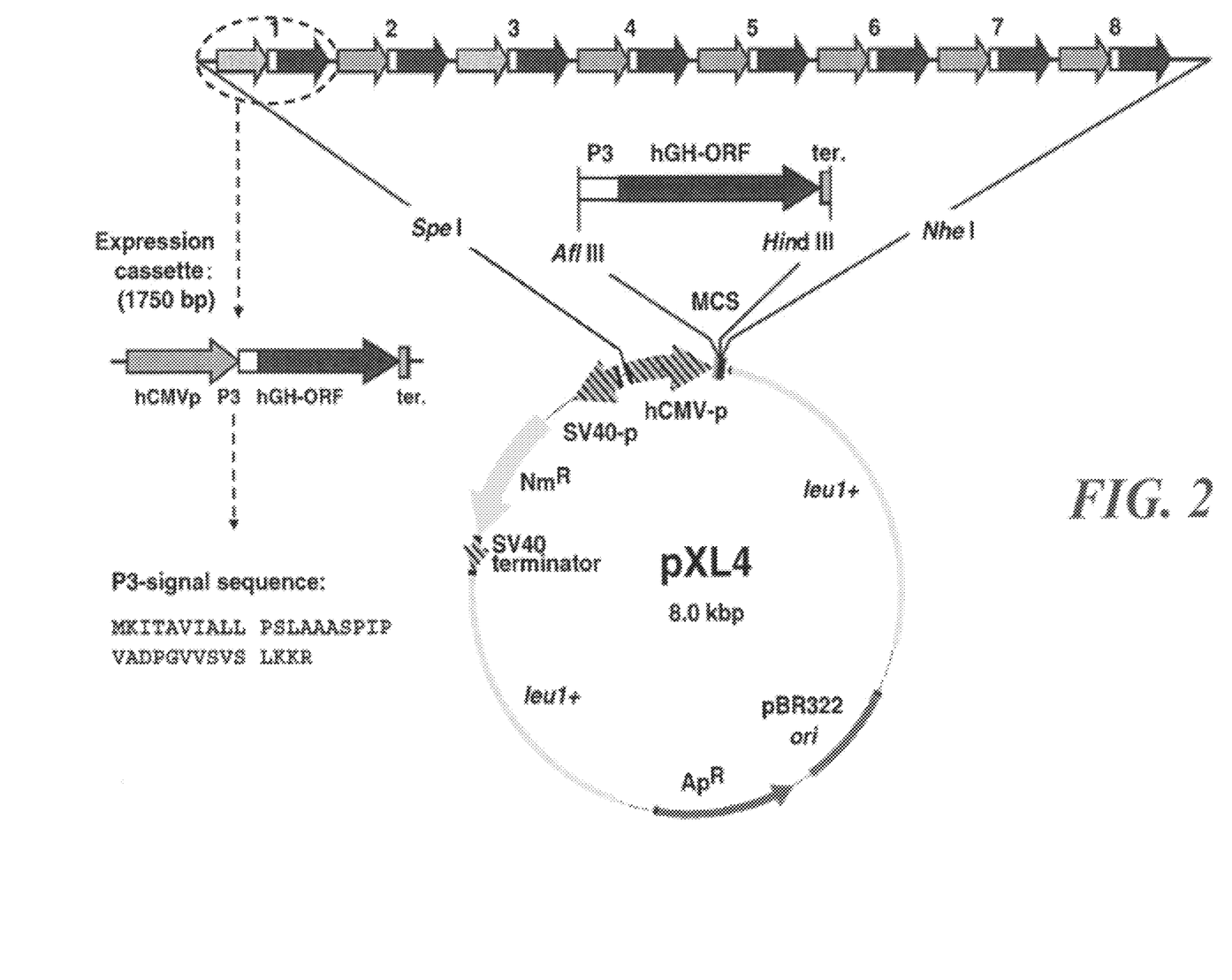
FIG. 2 The structure of a multiple expression cassette vector for expression of r-hGH.

FIG. 2 illustrates the structure of the multiple expression cassette vector constructed for secretory expression of r-hGH. The *S. pombe* high-bias codon-type hGH structural gene having AflII and BamHI sites at the termini was placed downstream of the P3 secretion signal sequence and inserted into the multicloning site (MCS) of the integrative expression vector pXL4. A SpeI site and a NheI site were placed at either terminus of the secretory expression cassette [hCMV-promoter-P3-hGHhb-terminator] in the resulting vector pTL2P3hGHhb(M5)-IXL to obtain the 8XL expression vector pTL2P3hGHhb(M5)-8XL. The two intergenic leu1+ gene sequences in the construct is were utilized to integrate the multiple expression cassettes into the leu1 locus of the host strain ARC001.

<Detection of r-hGH Secreted from the Transformant ARC001 (hGH)>

Secretion and degradation of r-hGH by the transformant ARC001 (hGH) obtained as described above were confirmed. The transformant was grown on YPD medium in glass tubes or 24-well plates at 32° C. with shaking, and 0.5-1.0 ml of the culture was withdrawn at various times.

The culture supernatants were subjected to a series of SDS-PAGE analysis after precipitation with TCA (10% trichloroacetic acid (final concentration)). The SDS-PAGE analysis was performed according to standard procedures under reductive conditions with 18% polyacrylamide gels (TEFCO). The gels were stained with CBB to detect hGH. From four clones, one positive clone was selected and stored at −80° C. in 25% glycerol.

Figure 3A:
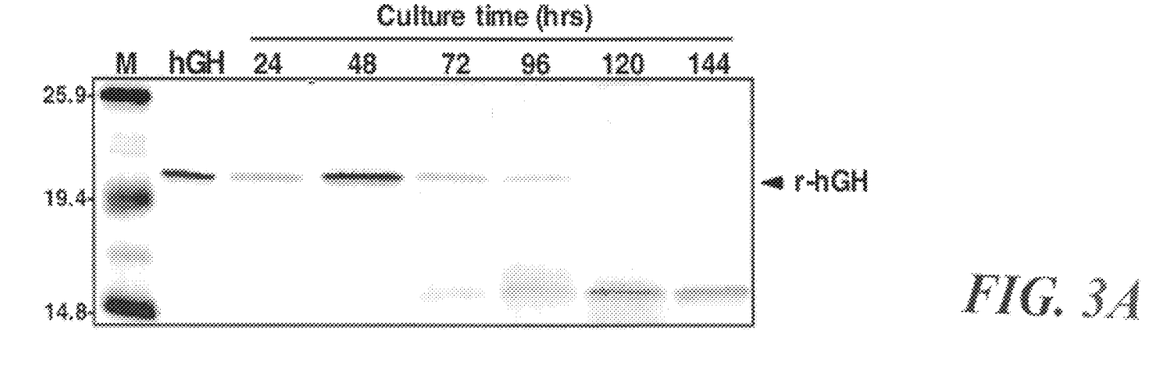

FIG. 3A shows the time-course analysis of r-hGH secretion from the transformant ARC001 (hGH): lane 1 is a molecular weight marker (unit: kilodalton); lane hGH is 1 g isolated intact human hGH; lanes 24-144 are 0.5 ml supernatants harvested from the transformant ARC001(hGH) at 24 to 144 hours subjected to SDS-polyacrylamide gel electrophoresis (SDS-PAGE) after precipitation with TCA. CBB (Coomassie brilliant blue) staining was used for detection.

The time-course analysis of r-hGH secretion by SDS-PAGE revealed that the apparent r-hGH secretion drastically decreased after 48 hours of cultivation as shown in FIG. 3A, indicating the possibility of proteolysis of the r-hGH secreted into the culture medium.

<Screening of hGH-Degrading Extracellular Proteases Using Protease Inhibitors>

Various proteases were added to a culture of the transformant obtained above to screen extracellular proteases for r-hGH degradation. The r-hGH-producing *S. pombe* strain ARC001[pTL2P3hGHhp(M5)-8XL] was subcultured in 20 ml YPD medium at 32° C. for 24 hours, and the 24-hour cell culture was transferred to a 24-well plate (1.0 ml/well) for screening of protease activity using a variety of protease inhibitors, except that at this stage, a portion of the culture supernatant was stored at −20° C. as the positive control. After addition of a variety of different protease inhibitors to the wells, the cells were incubated at 32° C. for 2 days with shaking. As the protease inhibitors, the 10 proteases contained in a protease inhibitor set (Roche Diagnostics) were added to the respective wells in given amounts, except for the negative control well. A 0.5 ml supernatant was collected from the cell culture in YPD medium in each well after 72 hours and 96 hours, concentrated by precipitation with TCA (10% w/v) and analyzed by SDS-PAGE.

Figure 3B:
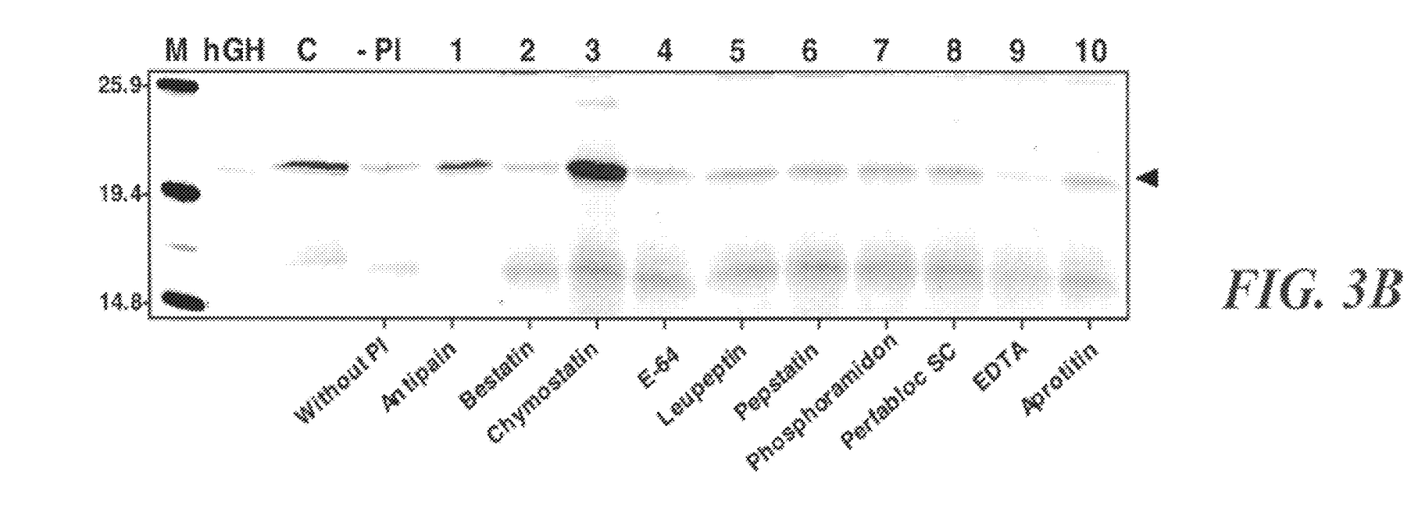

FIG. 3B shows the effect of each protease inhibitor in the culture of the transformant ARC001 (hGH) (time-course of r-hGH secretion) analyzed by SDS-PAGE (CBB staining). Lane M is a molecular weight marker (unit: kilodalton); Lane hGH is 0.5 μg native hGH; lane C is the control sample of the supernatant of the 24-hour culture in YPD medium withdrawn before addition of various proteases and stored at −20° C.; lane −PI is the control sample of the culture supernatant without protease inhibitor treatment; lanes 3-12 are samples of the culture supernatants treated with protease inhibitors.

The results revealed that addition of the inhibitor chymostatin to culture increased the 22-kDa major fragment from the secretory r-hGH, as shown in FIG. 3B. Addition of antipain slightly inhibited r-hGH degradation, too. Antipain inhibits papain-like cysteine proteases (such as papain) and some serine proteases such as trypsin and plasmin. Chymostatin inhibits mainly serine proteases with chymostatin-like specificity (such as chymotripsin, chymases and cathepsin G) and with some cysteine proteases including cathepsin B, H and L. This suggests the possibility that some unknown chymostatin-sensitive serine (and/or a few cysteine) proteases secreted into the culture (or onto the cell surface) are responsible for proteolysis during cultivation.

<Analysis of Secretory r-hGH from the Transformant ARC001 (hGH)>

The time-course of the level of secretory r-hGH from the transformant ARC001(hGH) was analyzed. Protease gene disruptants and ARC001 were transformed with the hGH expression vector, and 0.5 ml supernatants were withdrawn from the cultures of the transformants in YPD medium after 72 and 96 hours of cultivation, concentrated by TCA precipitation and analyzed by SDS-PAGE under reductive conditions on 18% polyacrylamide gels followed by staining with Coomassie brilliant blue R-250. Each strain is indicated by the deleted protease gene: As the molecular weight marker, Bench Mark prestained protein ladder (Invitrogen) was used. The results are shown in FIG. 4.

Figure 4:
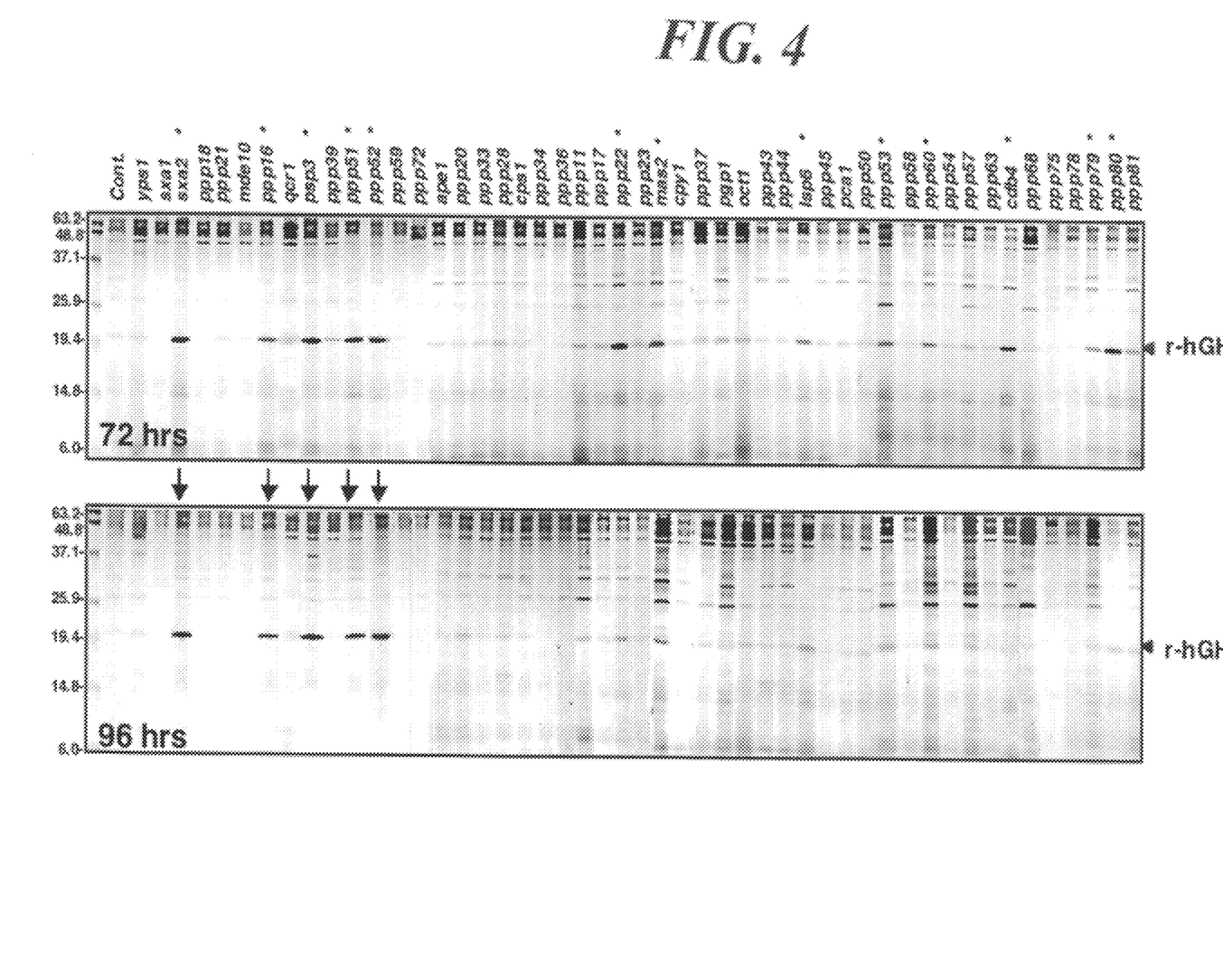
FIG. 4 SDS-PAGE showing r-hGH secretions at various times from protease gene disruptants and an ARC001 transformed with a hGH expression vector.

As is shown in FIG. 4, differences in secretory r-hGH level were observed among the ARC001 (hGH) transformants.

r-hGH degration was reduced in 12 ARC001 (hGH) transformants (*S. pombe* transformants in which protease genes sxa2, psp3, isp6, cdb4, ppp22, ppp51, ppp52, ppp60 or ppp79 gene was disrupted). Among these proteases, sxa2, psp3, isp6 and ppp7 are serine proteases, while cdb4, ppp22, ppp51, ppp52 and ppp60 belong to the metalloprotease gene family. Therefore, it is suggested that in addition to the expected serine proteases, some metalloproteases are involved in responsible for extracellular proteolysis of secretory r-hGH.

As shown in FIG. 4, the level of r-hGH expression was higher in the sxa2, psp3, pp 51 and ppp52 disruptants of *S. pombe*, which are indicated by arrows, than in other protease disruptants, and even higher than in a ppp16 disruptant (Examples in WO02/101038).

EXAMPLE 3

Construction of Multiple Protease Related Gene Disruptants of *S. pombe*

Among the 52 single protease related gene disruptants obtained by single disruption of proteases in *S. pombe* in Examples 1 and 2 (Non-patent Document 1), thirteen were chosen as the target protease genes for multiple disruption and listed in Table 2. The ORFs (open reading frames) of the protease genes listed in Table 2 were disrupted by the PCR-mediated homologous recombination (Non-patent Document 1) using a ura4 gene cassette as the selection marker. 200 to 300-bp sequences flanking the 5'- and 3'-termini of the target ORFs were amplified from the genomic DNA of the parental *S. pombe* strain ARC001 by two separate PCRs using appropriate gene adapter pairs designed so that the 5' and 3' termini fuse separately.

Then, by fusion extension PCR, the ura4 gene cassette was sandwiched between each pair of the resultant fusion PCR products to obtain protease gene disruption vectors (hereinafter referred to as gene disruption vectors).

*S. pombe* strain ARC010 was transformed with the gene disruption vectors. The transformed cells were grown on minimal medium, and colonies of uracil-unrequiring strains formed in the minimal medium (MMA+Leu plates) were obtained. Disruption of protease related genes in the strains was confirmed by colony PCR and DNA sequencing.

The confirmed protease related gene disruptants were grown on MMA+Leu+Ura+FOA medium, and colonies of uracil-requiring strains were harvested. Protease gene disruption was repeated on the harvested strains to give the multiple protease related gene disruptants shown in Table 3.

TABLE 3

List of multiple protease related gene disruptants of *S. pombe*

| Groups | | Disrupted protease genes in each strain | Strain name |
|---|---|---|---|
| A | A1 | psp3 | MGF241 |
|   | A2 | psp3– isp6 | MGF242 |
|   | A3 | psp3– isp6– ppp53 | MGF265 |
|   | A4-1 | psp3– isp6– ppp53– cdb4 | MGF279 |
|   | A4-2 | psp3– isp6– ppp53– ppp16 | MGF281 |
|   | A4-3 | psp3– isp6– ppp53– ppp51 | MGF280 |
|   | A5 | psp3– isp6– ppp53– ppp16– ppp22 | MGF311 |
|   | A6 | psp3– isp6– ppp53– ppp16– ppp22– sxa2 | MGF323 |
|   | A7-1 | psp3– isp6– ppp53– ppp16– ppp22– sxa2– pgp1 | MGF339 |
|   | A7-2 | psp3– isp6– ppp53– ppp16– ppp22– sxa2– ppp20 | MGF340 |
|   | A7-3 | psp3– isp6– ppp53– ppp16– ppp22– sxa2– ppp80 | MGF341 |
|   | A8 | psp3– isp6– ppp53– ppp16– ppp22– sxa2– ppp80– ppp20 | MGF433 |
| B | B3 | psp3– isp6– cdb4 | MGF264 |
|   | B4-1 | psp3– isp6– cdb4– sxa2 | MGF276 |
|   | B4-2 | psp3– isp6– cdb4– mas2 | MGF277 |
|   | B4-3 | psp3– isp6– cdb4– ppp51 | MGF278 |
|   | B5 | psp3– isp6– cdb4– sxa2– ppp52 | MGF317 |

<Measurement of Cell Growth Rate>

The growth rates of the resulting protease related gene disruptants of *S. pombe* were measured. Growth curves for the *S. pombe* strains were obtained using a biophotorecorder (TN-1506, Advantec). Cells were cultured in 5 ml YES medium in L-tubes at 32° C. with shaking. Turbidity was monitored every 5 minutes at an absorbance of 660 nm. The relative maximum growth rates ($\mu_{max}$) of 17 multiple protease disruptants were calculated using the $\mu_{max}$ value (0.26-0.30/H) for ARC001 strain as a control.

Figure 5:
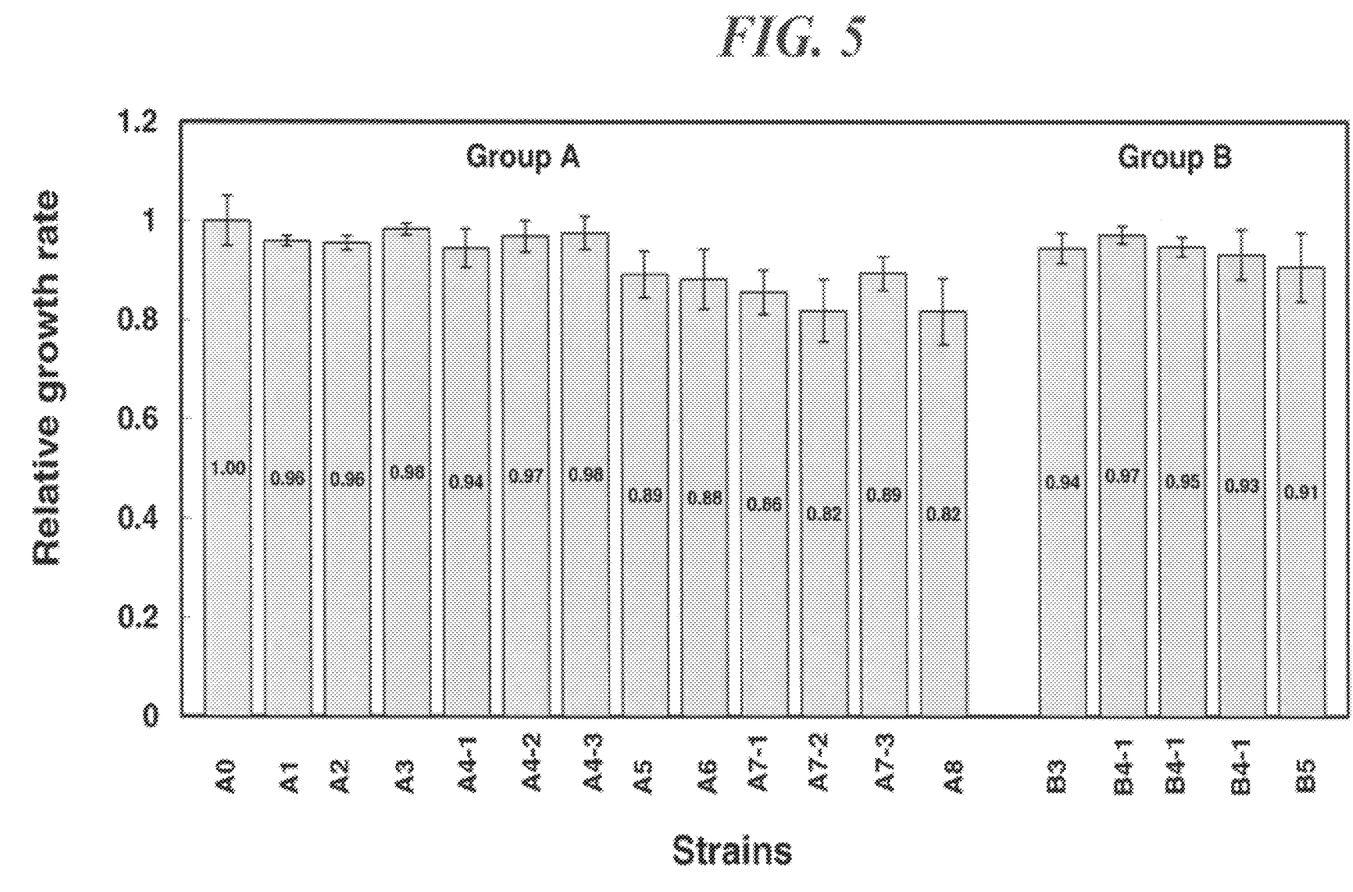
FIG. 5 A graph showing the relative growth rates of multiple protease-related gene disruptants from *S. pombe*.

FIG. 5 shows the relative maximum growth rates of the protease related gene disruptants. The relative $\mu_{max}$ value for each disruptant was calculated from the $\mu_{max}$ measurement for the disruptant using the $\mu_{max}$ value (0.26-0.30/H) for the ARC001 strain (indicated as A0) as a control. In the graph, the ordinate indicates relative $\mu_{max}$, while the abscissa indicates the strain names of the disruptants (listed in Table 3).

The results indicate that some protease genes affected cell growth rates. It turned out that for the sextuple and septuple disruptants, the relative growth rates were lower by about 10 to 20%, and the decrease was significant when both of the protease genes ppp22 and ppp20 were disrupted. Because the two genes had little effect on cell growth rate individually, it is suggested that multiple disruption of protease genes has

TABLE 2

List of protease genes (including putative genes) as targets for multiple disruption

| No. | Gene name | Systematic name | Descriptions | Protease family |
|---|---|---|---|---|
| 1 | Cdb4 | SPAC23H4.09 | Metallopeptidase | M24X |
| 2 | isp6 | SPAC4A8.04 | Subtilase-type proteinase | S8A |
| 3 | mas2 | SPBC18E5.12c | Mitochondrial processing peptidase α | M16B |
| 4 | pgp1 | SPCC1259.10 | Endopeptidase | M22 |
| 5 | ppp16 | SPBC1711.12 | Dipeptidyl peptidase | S9C |
| 6 | ppp20 | SPAC4F10.02 | Aspartyl aminopeptidase | M18 |
| 7 | ppp22 | SPBC14C8.03 | Methionine metallopeptidase | M24A |
| 8 | ppp51 | SPAC22G7.01c | Aminopeptidase | M24B |
| 9 | ppp52 | SPBC18A7.01 | Aminopeptidase | M24B |
| 10 | ppp53 | SPAP14E8.04 | Zinc metallopeptidase | M48B |
| 11 | ppp80 | SPAC19B12.08 | Peptidase | C54 |
| 12 | psp3 | SPAC1006.01 | Subtilase-type peptidase | S8A |
| 13 | sxa2 | SPAC1296.03c | Serine carboxypeptidase | S10 | combined effects. However, the decreases in growth rate were small on the whole at a level of from about 10 to 20% and are unlikely to affect the actual production. In order to examine whether the decrease in relative growth rate affects maximum cell density, the ultimate cell density of the multiple disruptant A8 (MGF433), which showed the lowest relative growth rate, in YES medium was actually determined after 4 days of incubation. It was found that on the contrary, the maximum OD (660 nm) for the octuple disruptant (A8) was larger by over 10% than that for the wild-type strain ARC001. The main reason is probably because at the sacrifice of growth rate, the multiple disruptant used nutrients efficiently, though slowly, for continued cell division without wasting them in ethanolic fermentation. Therefore, such enhanced cell growth is unlikely to hinder protein production.

EXAMPLE 4

Evaluation of Usefulness of Multiple Protease Disruptants by hGH Production

Examples 1 and 2 (Non-patent Document 1) describe evaluation of the usefulness of single protease disruptants using human growth hormone (hereinafter referred to as hGH), i.e., construction of the hGH-producing transformant ARC001 (hGH) and detection of the secretory hGH from the transformant ARC001 (hGH), its usefulness as a model heterologous protein for secretory production. In Example 4, usefulness of multiple protease disruptants was evaluated on the basis of secretory production of hGH as a heterologous protein model by experimentally examining inhibitory effect on multiple protease disruption on degradation of the product. Multiple protease disruptants were transformed with an integrative secretory hGH expression vector pTL2P3hGHhb (M5)-8XL described in Example 2 (Non-patent Document 1) by the lithium acetate method to make the multiple protease disruptants express hGH. Among six transformants, one clone which produced hGH most stably was selected, and hGH secretion was monitored. Further, reproducibility of the experiment was confirmed using other clones.

Especially, the time courses of hGH productions by some multiple disruptants from both groups were analyzed in detail by SDS-PAGE. The results are shown in FIG. 6.

Figure 6:
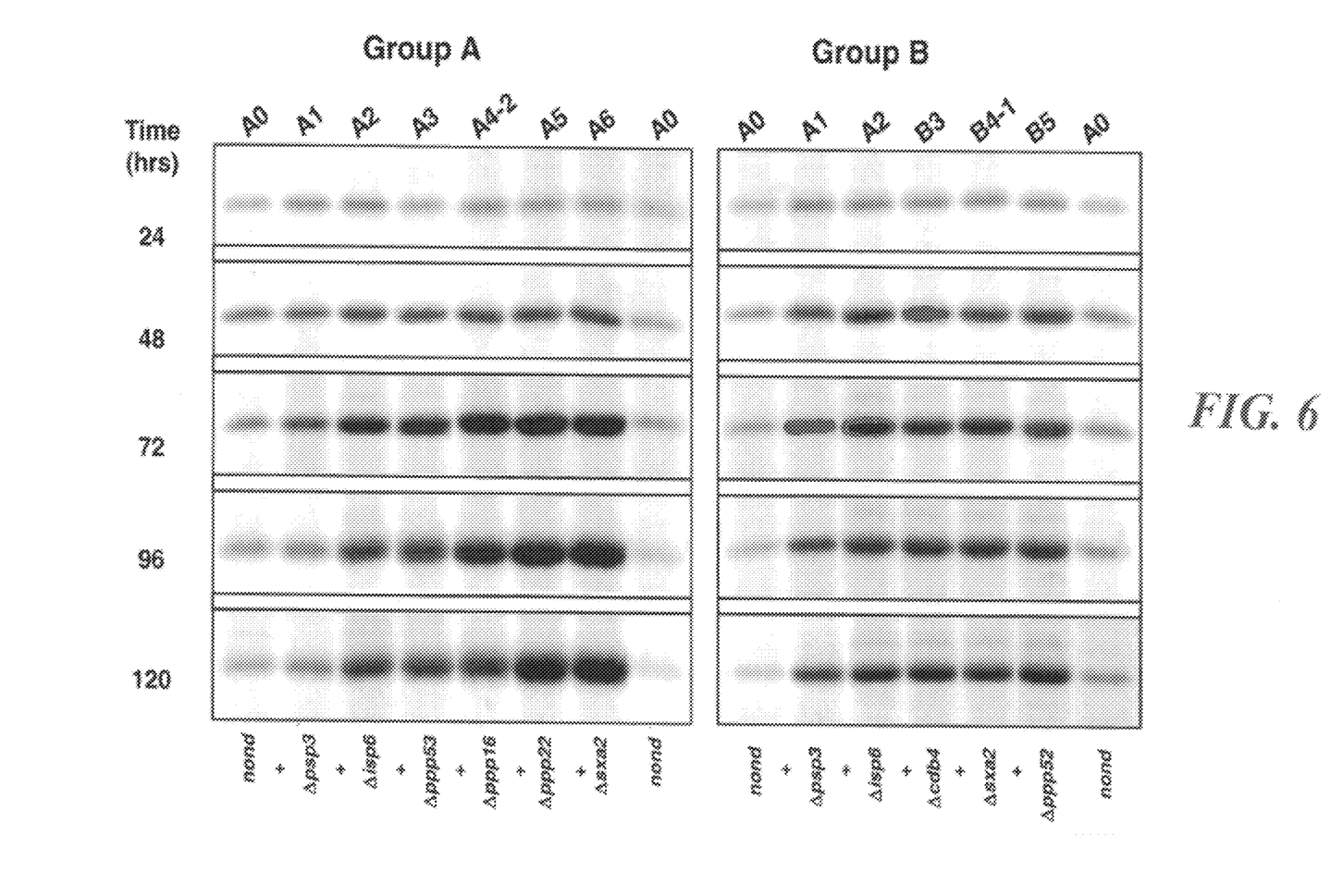
FIG. 6 SDS-PAGE showing hGH secretions from multiple protease-related gene disruptants from *S. pombe* at various times.

FIG. 6 shows the time course analysis of secretory hGH productions by multiple protease gene disruptants of *S. pombe* by SDS-PAGE. hGH secretions at various times were analyzed by SDS-PAGE (followed by Coomassie brilliant blue staining). A 0.5 ml supernatant was collected from the culture of each disruptant after given cultivation times, concentrated by precipitation with TCA and analyzed by SDS-PAGE. Above the respective lanes are the strain names of the disruptants (previously shown in Table 3), and below the lanes are the additively deleted protease related genes. Lane A0 (nond: non-disrupted strain) is the strain ARC001 with no disrupted protease genes.

The results of the SDS-PAGE analysis demonstrate that multiple protease related gene disruption led to remarkable increase in production of secretory hGH and clearly indicate that hGH production was almost the same among disruptants at 24 h but became appreciably different at 48 h and became clearly greater with the level of gene disruption. It is suggested that the basal hGH expression levels were almost similar among disruptants, and the difference in apparent expression level from 72 h onward was mainly attributed to the difference in hGH degradation. It turned out that the secretory hGH production in the non-disruptant A0 peaked at 48 hr and then drastically decreased, while the secretory hGH production in the multiple disruptants continued to increase until 72 h or 96 h, and the increase enhanced with the level of multiple disruption. Such a phenomenon was markedly observed in the multiple disruptants in Group A, and the high hGH levels were maintained until 120 h in the quintuple and sextuple disruptants A5 and A6. It is suggested that in multiple disruption, hGH degradation is slowed down more effectively as the number of disrupted protease related genes increases, but its effect is dependent of the combination of disrupted protease genes. Therefore, in multiple disruption of protease genes, it is important to try many disruption combinations and choose the best combination. In this respect, the present approach is proven to be useful.

Because in the above hGH expression experiments, there was little difference in effect between disruptants with more than five disrupted genes in Group A, experiments with the three septuple disruptants in Group A were carried out for an incubation time prolonged to 216 h. The SDS-PAGE results are shown in FIG. 7.

Figure 7:
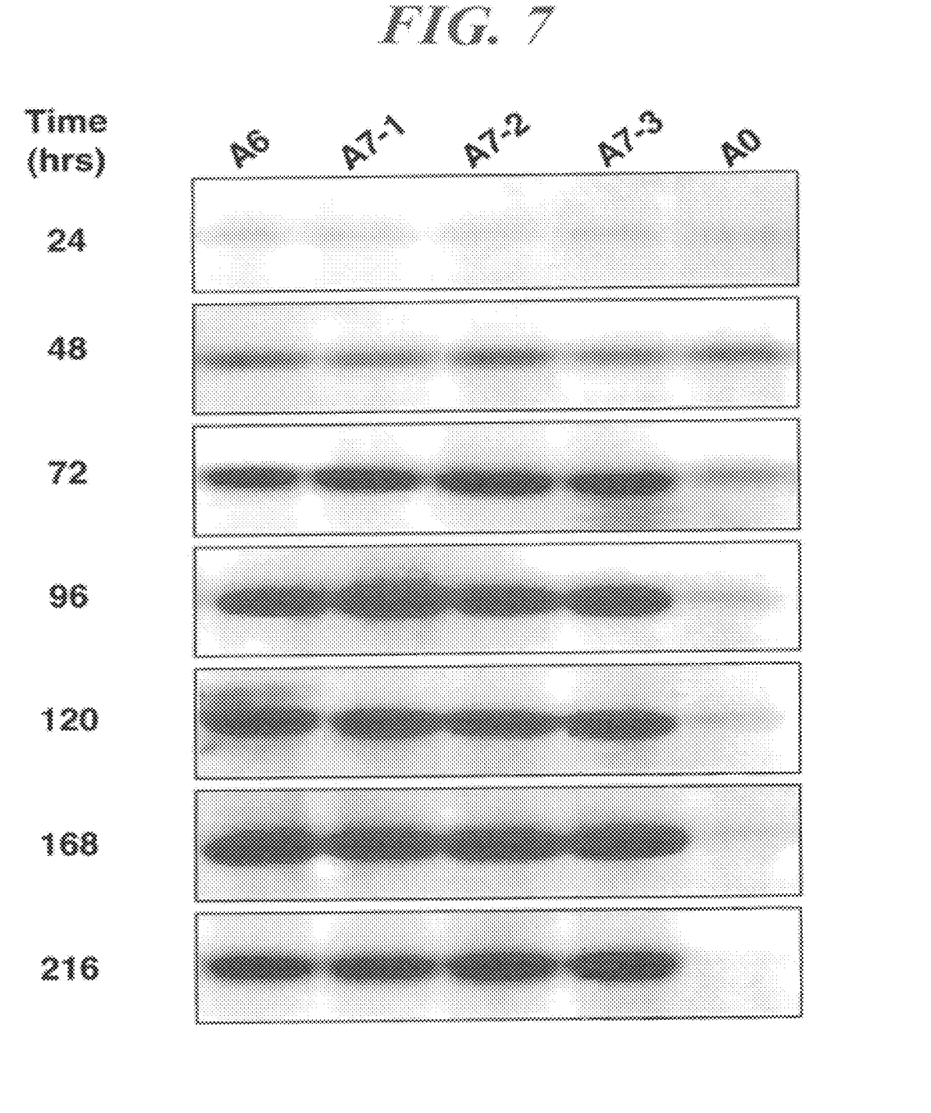
FIG. 7 SDS-PAGE showing hGH sections from a sextuple and septuple protease-related gene disruptants from *S. pombe* at various times.

FIG. 7 shows the results of time course analysis of the hGH secretions by sextuple and septuple protease disruptants of *S. pombe* by SDS-PAGE. A 0.5 ml supernatant was collected from the culture of each disruptant was collected after given cultivation times, concentrated by precipitation with TCA and analyzed by SDS-PAGE (followed by Coomassie brilliant blue staining). Above the respective lanes are the strain names of the disruptants (previously shown in Table 3). Lane A0 (nond: non-disrupted strain) is the strain ARC001 with no disrupted protease genes.

The results indicate that the septuple disruptants and the sextuple disruptant were similarly effective and did not differ much in secretory hGH production until 216 h. The experimental system employed has its detection limit and could hardly prove the difference between sextuple and higher disruptants in effectiveness. The difficulty may be solved by an experimental system using a more protease-sensitive heterologous protein as the model protein.

INDUSTRIAL APPLICABILITY

In the present invention, the efficiency of production of a heterologous protein by a transformant of the fission yeast *S. pombe* is improved by deleting or inactivating one or more protease-related genes in the host cells. Such a protease disruptant can be widely used for production of protease-sensitive heterologous proteins.

The entire disclosures of Japanese Patent Application No. 2005-225638 filed on Aug. 3, 2005 and Japanese Patent Application No. 2006-160347 filed on Jun. 8, 2006 including specifications, claims, drawings and summaries are incorporated herein by reference in their entireties.

What is claimed is:

1. A mutant *Schizosaccharomyces pombe* cell that has a deletion or inactivation of at least three endogenous target genes whereby the level of expression of a gene encoding a heterologous protein in said mutant *Schizosaccharomyces pombe* host cell is higher compared to a corresponding *Schizosaccharomyces pombe* cell that does not have a deletion or inactivation of the at least three endogenous target genes;
   (i) wherein at least one of the deleted or inactivated target genes is selected from the group consisting of cdb4 (SPAC23H4.09), and ppp53 (SPAP 14E8.04); and
   (ii) wherein at least two of the deleted or inactivated target genes are selected from the group consisting of isp6 (SPAC4A8.04), ppp16 (SPBC 1711.12), psp3 (SPAC 1006.01) and sxa2 (SPAC 1296.03c).

2. The mutant *Schizosaccharomyces pombe* cell of claim 1, wherein cdb4 (SPAC23H4.09) is deleted or inactivated.

3. The mutant *Schizosaccharomyces pombe* cell of claim 1, wherein ppp53 (SPAP 14E8.04) is deleted or inactivated.

4. The mutant *Schizosaccharomyces pombe* cell of claim 1, wherein ppp53 (SPAP14E8.04) is deleted or inactivated and wherein isp6 (SPAC4A8.04) and psp3 (SPAC 1006.01) are deleted or inactivated.

5. The mutant *Schizosaccharomyces pombe* cell of claim 1, wherein ppp53 (SPAP14E8.04) is deleted or inactivated and wherein isp6 (SPAC4A8.04), psp3 (SPAC 1006.01) and ppp16 (SPBC 1711.12) are deleted or inactivated.

6. The mutant *Schizosaccharomyces pombe* cell of claim 1, wherein ppp53 (SPAP 14E8.04) is deleted or inactivated and wherein isp6 (SPAC4A8.04), psp3 (SPAC 1006.01), ppp16 (SPBC 1711.12) and ppp22 (SPBC 1408.03) are deleted or inactivated.

7. A method for expressing a heterologous protein in a mutant *Schizosaccharomyces pombe* comprising expressing a gene encoding a heterologous protein in a mutant *Schizosaccharomyces pombe* host cell in which at least three target genes are deleted or inactivated whereby the level of expression of the gene encoding the heterologous protein in said mutant *Schizosaccharomyces pombe* host cell is higher compared to a corresponding *Schizosaccharomyces pombe* cell that does not have a deletion or inactivation of the at least three endogenous target genes;
 (i) wherein at least one of the deleted or inactivated target genes is selected from the group consisting of cdb4 (SPAC23H4.09) and ppp53 (SPAP 14E8.04);
 (ii) wherein at least two of the deleted or inactivated target genes is selected from the group consisting of isp6 (SPAC4A8.04), ppp16 (SPBC 1711.12), psp3 (SPAC1006.01), and sxa2 (SPAC 1296.03c); and culturing said mutant *Schizosaccharomyces pombe* host cell under conditions suitable for production of the heterologous protein, and optionally, for its secretion into the culture medium, and recovering the heterologous protein.

8. The method of claim 7, wherein at least one of the target genes has been deleted.

9. The method of claim 7, wherein at least one of the target genes has been inactivated.

10. The method of claim 7, wherein said at least one target gene has been deleted or inactivated by replacing an open reading frame (ORF) of said gene with a marker gene.

11. The method of claim 7, wherein cdb4 (SPAC23H4.09) is deleted or inactivated.

12. The method of claim 7, wherein ppp53 (SPAP14E8.04) is deleted or inactivated.

13. The method of claim 7, wherein ppp53 (SPAP 14E8.04), isp6 (SPAC4A8.04) and psp3 (SPAC 1006.01) are deleted or inactivated.

14. The method of claim 7, wherein ppp53 (SPAP 14E8.04), isp6 (SPAC4A8.04), psp3 (SPAC 1006.01) and ppp16 (SPBC 1711.12) are deleted or inactivated.

15. The method of claim 7, wherein ppp53 (SPAP 14E8.04), isp6 (SPAC4A8.04), psp3 (SPAC 1006.01), ppp16 (SPBC 1711.12) and ppp22 (SPBC 14C 8.03) are deleted or inactivated.

16. The method of claim 7, wherein the heterologous protein is human growth hormone (hGH) and wherein the level of expression of the gene encoding said human growth hormone (hGH) protein in said mutant *Schizosaccharomyces pombe* host cell is higher compared to a corresponding *Schizosaccharomyces pombe* cell that does not have a deletion or inactivation of the at least three endogenous target genes.

* * * * *